United States Patent [19]

Schmolka

[11] 4,326,977

[45] Apr. 27, 1982

[54] LIQUID ANTISEPTIC CLEANERS WITH IMPROVED FOAMING PROPERTIES

[75] Inventor: Irving R. Schmolka, Grosse Ile, Mich.

[73] Assignee: BASF Wyandotte Corporation, Wyandotte, Mich.

[21] Appl. No.: 205,115

[22] Filed: Nov. 10, 1980

[51] Int. Cl.³ .................... C11D 1/722; C11D 3/48; C11D 17/08
[52] U.S. Cl. ................... 252/106; 252/173; 252/174.21; 252/351; 252/DIG. 14
[58] Field of Search ............... 252/106, 107, 174.21, 252/174.22, 351, 173; 424/326

[56] References Cited
U.S. PATENT DOCUMENTS

| | | | |
|---|---|---|---|
| Re. 29,909 | 2/1979 | Kurtz | 252/106 |
| 2,828,345 | 3/1958 | Spriggs | 252/174.21 |
| 3,855,140 | 12/1974 | Billany | 252/106 |
| 3,960,745 | 6/1976 | Billany | 252/106 |
| 3,997,458 | 12/1976 | Kurtz | 252/106 |
| 4,200,733 | 4/1980 | Perner | 252/106 |

*Primary Examiner*—Dennis L. Albrecht
*Attorney, Agent, or Firm*—Bernhard R. Swick

[57] ABSTRACT

A skin cleansing composition comprising an antiseptic agent, a polyoxyethylene-polyoxybutylene block copolymer wherein the polyoxybutylene portion of the compound has a molecular weight of from 500 to 2000 and the polyoxyethylene portions contribute from about 60 to 90 percent by weight of the compound and water.

12 Claims, No Drawings

LIQUID ANTISEPTIC CLEANERS WITH IMPROVED FOAMING PROPERTIES

BACKGROUND OF THE INVENTION

1. Field of the Invention

This invention relates to cleansing compositions and in particular it relates to such compositions, containing an antibacterial compound and a surfactant which are suitable for skin cleansing. The compositions of the invention are useful in surgical practice as a pre-operative scrub; and may be used routinely by hospital ward staff.

2. Description of the Prior Art

The essential constituents in this type of cleaning composition are an antiseptic agent and a surfactant. An antiseptic agent which, in recent years, has come to the fore as particularly effective is chlorhexidine, i.e., 1,6-di-(4-chlorophenyldiguanido)hexane, and salts thereof. However, many common surfactants are incompatible with many antiseptic agents, particularly chlorhexidine. Thus, anionic surfactants are known to destroy the antibacterial activity of chlorhexidine solutions by complexing with the cationic chlorhexidine, and cationic surfactants are not preferred because of their irritancy, and because, in combination with a soluble chlorhexidine salt, double decomposition can occur with the formation of insoluble chlorhexidine salts and consequent loss of antibacterial activity. Amphoteric surfactants, which contain either anionic or cationic centers, depending upon pH, suffer from the above-described disadvantages of anionic and cationic surfactants, and are therefore equally unsuitable for the present purpose.

U.S. Pat. No. 3,960,745, a continuation of U.S. Pat. No. 3,855,140, discloses such cleansing compositions containing a soluble salt of chlorhexidine, a polyoxyethylene-polyoxypropylene block co-polymer and an inert diluent or carrier. Particularly preferred block copolymers are those sold under the trademark Pluronic, particularly the Pluronic P-84, P-85 and F-87 surfactants. However, this patent indicates in column 2 that for user acceptability, it is necessary to include an additional foaming agent in order to get adequate foaming. The patent says, "Most foaming agents deactivate chlorhexidine to a large extent, but with amine oxide foaming agents the deactivation is kept to a minimum. Nevertheless, some deactivation is unavoidable, so it is preferable to use a surfactant having maximum foaming properties so that the quantity of deactivating foaming agent is kept to a minimum."

The patent indicates that Pluronic polyols P-84, P-85 and F-87 have the greatest foaming ability and with these the addition of 3.75 percent of an amine oxide foaming agent gives a composition having acceptable foaming properties but that with other Pluronic polyols, it is necessary to increase the quantity of additional foaming agent and to increase also the quantity of chlorhexidine in order to overcome the deactivating effect of additional foaming agent.

All the preferred Pluronic polyols of the patent have a hydrophobe molecular weight of 2250 and contain between 40 and 70 percent polyoxyethylene groups by weight. It is known from the published literature of the BASF Wyandotte Corporation that increasing or decreasing the hydrophobe molecular weight decreases the foaming properties of the Pluronic polyols alone. Accordingly, it would be desirable to have a cleansing composition employing an antiseptic agent and a nonionic surfactant which requires less and preferably no additional foaming agent even when said surfactant has a considerably lower molecular weight than 2250 for the hydrophobic group.

U.S. Pat. No. Re. 29,909 discloses aqueous detergent solutions of block copolymers of PO-EO such as the Pluronic polyols which may contain antiseptic agents. The Pluronic polyols employed should have an ethylene oxide content of at least 75 percent, the antiseptic agents disclosed do not include chlorhexidine.

U.S. Pat. No. 2,828,345 discloses products prepared by first condensing butylene oxide with a butylene glycol to form a polyoxybutylene glycol having a molecular weight greater than 1000 and thereafter condensing ethylene oxide with the polyoxybutylene glycol until the so-prepared product has an oxyethylene content of from 20 to 90 percent by weight. Suitable butylene oxides listed include, 1,2-butylene oxide.

U.S. Pat. No. 4,200,733 discloses block copolymers which contain from 5 to 25 percent by weight of bonded iodine and which are based on iodine-free compounds which are block polymers of (A) a polymer or copolymer block of from 4 to 100, 1,4-butylene oxide units, and from 0 to 25 ethylene oxide units, and (B) a copolymer block of from 0 to 50 1,4-butylene oxide units and from 1 to 100 ethylene oxide units, the proportion of 1,4-butylene oxide being greater than 50 mole percent in (A) and less than 50 mole percent in (B).

For a skin cleansing composition containing an antibacterial compound, it is necessary to have a composition that exhibits high foaming, as previously pointed out, together with good solubility in water, non-irritancy to the skin, and adequate detergency.

SUMMARY OF THE INVENTION

It has been found in accordance with the instant invention that the above object may be achieved and particularly higher foaming cleaning compositions may be achieved with polyoxyalkylene nonionic agents having lower molecular weight in the hydrophobe than with prior art compositions without the aid of additional foaming agents or with reduced quantities thereof. More specifically, the cleaning solution of the instant invention comprises an aqueous detergent solution containing, as the detergent, a block copolymer that consists of water-soluble poly(oxyethylene) groups at both ends of a water-insoluble poly(oxybutylene) chain. The terminal polyoxyethylene groups represent 60 to 90 percent by weight of the molecule and the polyoxybutylene hydrophobe has a molecular weight ranging from 500 to 2000. This invention includes cleaning fluids and concentrates which can be diluted with water, as a base to prepare cleaning fluids.

DESCRIPTION OF THE PREFERRED EMBODIMENTS

The preferred polyoxybutylene-polyoxyethylene block copolymers have the general formula:

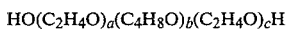

$$HO(C_2H_4O)_a(C_4H_8O)_b(C_2H_4O)_cH$$

wherein $a+c$ equals 60 to 90 percent of the total weight of the copolymer and b represents a molecular weight of the polyoxybutylene portion of the polymer molecule which is between 500 and 2000. The block copolymers of the invention are members of a family comprised of an almost unlimited number of nonionic surfactants in a series of block copolymers that consists of water-soluble poly(oxyethylene) groups at both ends of a water-insoluble poly(oxybutylene) chain.

The first step in making the surfactants employed in the present invention is the controlled addition of butylene oxide at the two hydroxyl groups of a monomeric diol, preferably butylene glycol and most preferably 1,4-butylene glycol. It is also preferred to employ 1,2-butylene oxide for the addition to the two hydroxyl groups of the 1,4-butylene glycol nucleus. At the higher molecular weights, the resulting polyoxybutylene glycol becomes water-insoluble to form a hydrophobe which is then tailored to the desired molecular weight, i.e., 500 to 2000, and ethylene oxide is added to sandwich the hydrophobic base between hydrophilic poly(oxyethylene) groups which are controlled in length. The surfactants employed in the present invention are members of the group in which the ethylene oxide addition is controlled to constitute from 60 to 90 percent by weight of the final molecule.

The hydrophobic oxybutylene chains may optionally, but advantageously, contain small amounts of ethylene oxide and/or propylene oxide and may partially replace the butylene oxide to provide a ratio in the predominantly oxybutylene hydrophobic chains of ethylene oxide and/or propylene oxide groups to butylene oxide groups of from about 1:20 to about 1:3. Similarly, the oxyethylene hydrophilic chains may also optionally, but advantageously, contain small amounts of alkylene oxides such as propylene oxide and butylene oxide which may partially replace the ethylene oxide units whereby the ratio of propylene oxide and/or butylene oxide to ethylene oxide in the hydrophilic chains may range from 1:20 to 1:4, preferably 1:20 to 1:9.

It is to be understood that the expression polyoxyethylene-polyoxybutylene block copolymer, which corresponds to the above formula, includes such amounts of propylene oxide and/or ethylene oxide groups in the hydrophobic polyoxybutylene chains and such amounts of propylene oxide and/or butylene oxide groups with the hydrophilic polyoxyethylene chains.

A more detailed disclosure of the preparation of the surfactants can be found, for instance, in U.S. Pat. No. 2,828,345, hereby incorporated by reference.

The surfactants employed in this invention are all water-soluble and thus, the cleansing solutions employed in the invention may be prepared by simply dissolving the copolymer in water.

The antiseptic employed in the instant composition can be any of the known antiseptic agents which are soluble to the extent of at least about 0.5 percent w/v in water at ambient temperature, particularly those conventionally included in surgical scrub solutions. Such antiseptic agents include, for example, benzalkonium chloride, chloramine, iodine, iodophors such as polyvinyl pyrrolidoneiodine, and chlorhexidine and salts thereof. Suitable salts of chlorhexidine which are soluble in water at ambient temperature to the extent of at least 0.5 percent w/v are, for example, the gluconate, isethionate (2-hydroxyethanesulphonate), formate, acetate, glutamate, succinamate, monoglycollate, dimethanesulfonate, lactate, di-isobutyrate and glucoheptonate, and of these, the gluconate is particularly preferred. Chlorhexidine and the salts thereof, particularly the gluconate, are the preferred antiseptics of this invention. Other antiseptics include parachloro meta xylenol, hexachlorophene, 2-bromo-2-nitropropane diol, salicylanilide, didecyl dimethyl ammonium chloride, cetyl dimethylethyl ammonium bromide, alkyl dimethyl benzyl ammonium chloride, alkyl dimethylethyl benzyl ammonium chloride, alkyl dimethylbenzyl ammonium succinate, alkyl dimethyl-3,4-dichlorobenzyl ammonium chloride, 3,3',4',5-tetrachlorosalicylanilide, 3',4',5-trichlorosalicylanilide, 3,5-dibromo-3'-trifluoromethylsalicylanilide, and 3,4,4'-trichlorocarbamilide.

Suitable concentrate compositions can be prepared comprising from about 0.5 to 10.0 percent w/v, preferably 0.5 to 5.0 percent w/v of the antiseptic and about 5 to 40 percent w/v, preferably 10 to 30 percent w/v of the polyoxybutylene-polyoxyethylene block copolymer as above described, balance water. Additives normally found in such cleaning compositions may also be employed. Also, normal cleaning solution impurities in normal amounts may also be present.

These concentrates are typically diluted with water in the proportion of 1:10,000 to 1:10 to provide the cleaning compositions. The ultimate cleaning composition comprises from about $5 \times 10^{-5}$ to 1.0 percent w/v preferably $5 \times 10^{-4}$ to $5 \times 10^{-2}$ percent w/v of the antiseptic and about $5 \times 10^{-4}$ to 4.0 percent w/v, preferably $5 \times 10^{-3}$ to $3 \times 10^{-1}$ percent w/v of the nonionic surfactant balance water and possibly conventional additives in usual amounts.

For user acceptability, the compositions should possess good foaming properties. One of the principal advantages of the instant composition is that it generally possesses good foaming properties without the addition of other foaming agents that tend to deactivate chlorhexidine thereby requiring more chlorhexidine. However, in some instances, it may be necessary or desirable to employ a small amount of another foaming agent such as an amine oxide foaming agent. Nevertheless, in any event, the compositions of the instant invention employing polyoxyethylene capped polyoxybutylene compounds generally require less of such additional foaming agent than with similar compounds, (i.e., comparable hydrophobe molecular weight and percent alkylene oxide groups) having a polyoxypropylene nucleus as disclosed in U.S. Pat. Nos. 3,960,745; 3,855,140, and U.S. Pat. No. Re. 29,909. This is unexpected since there is nothing in any of the prior art, including U.S. Pat. No. 2,828,345, to suggest that polyoxybutylene containing nonionic copolymers would have higher foaming properties for a given hydrophobe molecular weight and percentage ethylene oxide than that achieved in similar compounds having a polyoxypropylene nucleus.

The compositions in accordance with the instant invention may also optionally contain conventional additives such as perfumes, coloring agents and preservatives, for example, isopropyl alcohol, ethyl alcohol, methyl p-hydroxybenzoate, or propyl p-hydroxylbenzoate. It is also advantageous to adjust the pH of the composition to between 5 and 7, preferably about 5.5 to minimize the precipitation of insoluble antiseptic agents on storage. A suitable agent for adjusting the pH of the compositions is, for example, gluconolactone, or the acid from which the anion of the chlorhexidine salt is derived.

The following examples are included to further illustrate the present invention.

EXAMPLE 1

A solution comprising by weight 20 parts of a 20 percent w/v aqueous solution of chlorhexidine gluconate, 20 parts of a nonionic surfactant (100 percent active) designated herein as nonionic no. 1, and 60 parts of sterile water was prepared by stirring the above ingredients in a suitable container until everything is dissolved. Nonionic no. 1 defines a polyoxyethylene adduct of a polyoxybutylene hydrophobic base having a molecular weight of said base of about 1100 and wherein the oxyethylene content is about 80 percent by weight of the molecule. The polyoxybutylene hydrophobic base is prepared by reacting 1,2-butylene oxide with a 1,4-butylene glycol initiator.

The solution was diluted to a ratio by weight of 1:1024 with water and tested against *Staphylococcus aureus* and *Escherichia coli* by the following test.

Soak 30 one-half inch diameter disks of very pure highly absorbent paper with the above-described diluted solution.

Prepare 5 replicate plates for each organism (i.e., 2×5 or total of 10 plates). Separately innoculate two flasks containing 150 milliliters of sterile liquid nutrient Agar B (at temperature equal to or less than 40° C.), with 1 milliliter of 24-hour nutrient broth culture of *S. aureus* and *E. coli* respectively. Vigorously swirl contents of each flask to insure complete mixing. Add 10 milliliter portions of innoculated agar to each of the five 100-milliliter sterile petri dishes for each organism, distribute evenly and let cool and harden. As soon as the plates harden, implant three of the paper disks soaked with cleaning solution on the center of each test agar plate surface. Using blunt forceps, press each disk onto the agar surface to insure complete and uniform contact. Incubate test plates 48 hours at 37° C. Following incubation, examine test plates to determine presence or absence of zones of inhibition around the circumference of each of the test disks.

A detectable zone of inhibition of 0.1 millimeters or greater was obtained, demonstrating that there was no significant reduction of antimicrobial activity of the chlorhexidine gluconate by the nonionic surfactant with respect to these common micro-organisms.

EXAMPLES 2–5

Examples illustrating superior foaming properties of the composition of the instant invention as compared to an otherwise identical composition employing Pluronic F-87 polyol which is indicated in U.S. Pat. No. 3,960,745 as one of the Pluronic polyols having the greatest foaming ability are provided in Table I below. All three of these preferred Pluronic polyols, i.e., P-84, P-85 and F-87, of this patent have a molecular weight of the polyoxypropylene group of 2200

Two compositions were employed for each example which are indicated in Table I as composition #1 and composition #2, and two samples of each composition for each example were tested in a Bacon foam machine, one at 25 rpm and the other at 45 rpm.

The compositions indicated under No. 1 are solutions consisting of 12.5 percent by weight of the nonionic, 12.5 percent by weight of a 20 percent w/v aqueous solution of chlorhexidine gluconate, balance water. The compositions indicated under No. 2 are solutions comprising 6.25 percent by weight of the nonionic surfactant, 6.25 percent by weight of the above chlorhexidine gluconate solution, balance water.

In performing the test with the Bacon foam machine, 200 milliliters of the test solution is placed in a two and one-fourth inch internal diameter 1000 milliliter graduate, which is equipped with a ground glass stopper. The graduate is closed with the stopper and placed in a gripping device attached to the shaft of a motor with the axis of the graduate at right angles to the motor shaft. One 200 milliliter sample for each of Composition No. 1 and Composition No. 2 is rotated at 25 rpm, with the temperature at 25° C. for 1 minute. A second 200 milliliter sample for each of Composition No. 1 and No. 2 is rotated at 45 rpm at 25° C. for 1 minute. The initial foam height for each sample of each composition is observed immediately after rotation is stopped and at one minute and two minute intervals and the results set forth in Table I below.

TABLE I

| Example No. | Nonionic | Time | Composition No. 1 | | Composition No. 2 | |
|---|---|---|---|---|---|---|
| | | | 25 rpm. | 45 rpm. | 25 rpm. | 45 rpm. |
| 2 (comparative) | Pluronic F-87 | Initial | 0 @ 10 sec. | 130 mls | 300 mls | 400 mls |
| | | 1 min. | — | 0 @ 30 sec. | 0 @ 22 sec. | 0 @ 45 sec. |
| | | 2 min. | — | — | — | — |
| 3 | 1 | Initial | 130 mls | 180 mls | 380 mls | 490 mls |
| | | 1 min. | 120 mls | 170 mls | 220 mls | 350 mls |
| | | 2 min. | 110 mls | 170 mls | 200 mls | 240 mls |
| 4 | 2 | Initial | 130 mls | 130 mls | 300 mls | 380 mls |
| | | 1 min. | 110 mls | 130 mls | 210 mls | 240 mls |
| | | 2 min. | 0 @ 1'5" | 110 mls | 210 mls | 220 mls |
| 5 | 3 | Initial | 110 mls | 120 mls | 300 mls | 350 mls |
| | | 1 min. | 110 mls | 110 mls | 200 mls | 200 mls |
| | | 2 min. | 0 | 110 mls | 200 mls | 200 mls |

From the above, it can be clearly seen that all the compositions employing the polyoxybutylene containing nonionics have greatly superior foam stability to the composition containing Pluronic F-87 polyol.

The nonionic surface-active agents indicated by the numbers ranging from 1 to 3 in Table I are as follows:

Nonionic 1 is the same as described above in connection with Example 1.

Nonionic 2 defines the polyoxyethylene adduct of a polyoxybutylene hydrophobic base having a molecular weight of about 1600 wherein the oxyethylene content is about 70 weight percent of the molecule.

Nonionic 3 defines the polyoxyethylene adduct of a polyoxybutylene hydrophobic base having a molecular weight of about 1600 wherein the oxyethylene content is about 80 weight percent of the molecule.

Like Nonionic No. 1, Nonionics 2 and 3 have a polyoxybutylene hydrophobic base of 1,2-butylene oxide units on a 1,4-butylene glycol initiator.

EXAMPLE 6

Example 1 is repeated with the exception that didecyldimethyl ammonium chloride is employed in lieu of the chlorhexidine gluconate.

EXAMPLE 7

Example 1 is repeated with the exception that the composition also includes a perfume, isopropyl alcohol and gluconolactone.

EXAMPLE 8

Example 2 is repeated with the exception that cetyldimethylethyl ammonium bromide is employed in lieu of chlorhexidine gluconate.

EXAMPLE 9

Example 2 is repeated with the exception that 3,3′,4′,5-tetrachlorosalicylanilide is employed in lieu of chlorhexidine gluconate.

EXAMPLE 10

Example 2 is repeated with the exception that benzalkonium chloride is employed in lieu of chlorhexidine gluconate.

EXAMPLE 11

Example 2 is repeated with the exception that polyvinyl pyrrolidone iodine is employed in lieu of chlorhexidine gluconate.

The embodiments of the invention in which an exclusive privilege or property is claimed are defined as follows:

1. A skin cleansing composition having good foaming properties comprising an agent selected from the group consisting of parachloro meta xylenol, hexachlorophene, 2-bromo-2-nitropropane diol, salicylanilide, didecyl dimethyl ammonium chloride, cetyl dimethylethyl ammonium bromide, alkyl dimethyl benzyl ammonium chloride, alkyl dimethylethyl benzyl ammonium chloride, alkyl dimethylbenzyl ammonium succinate, alkyl dimethyl-3,4-dichlorobenzyl ammonium chloride, 3,3′,4′,5-tetrachlorosalicylanilide, 3′,4′,5-trichlorosalicylanilide, 3,5-dibromo-3′-trifluoromethylsalicylanilide, 3,4,4′-trichlorocarbamilide, benzalkonium chloride, chloramine, iodine, iodophors, chlorhexidine and salts thereof, in normal antiseptic amounts agent, a polyoxyethylene-polyoxybutylene block copolymer wherein the polyoxybutylene portion of the compound has a molecular weight of from 500 to 2000 and the polyoxyethylene portions contribute from about 60 to 90 percent by weight of the compound in an amount of from 5 to 40 percent w/v and the balance substantially water.

2. The composition of claim 1 wherein said polyoxyethylene-polyoxybutylene block copolymer has the formula: Ps $$HO(C_2H_3O)_a(C_4H_8O)_b(C_2H_4O)_cH$$

wherein a, b and c are integers such that the copolymer consists of 60 to 90 percent by weight polyoxyethylene groups and wherein the molecular weight of the polyoxybutylene groups is about 500 to 2000.

3. The composition of claim 2 wherein said antiseptic is a chlorhexidine compound.

4. The composition of claim 2 wherein said cleansing composition is a concentrate consisting essentially of about 0.5 to 10 percent w/v of antiseptic agent, 5 to 40 percent w/v said block copolymer, and 95 to 50 percent by weight water.

5. The composition of claim 4 wherein said antiseptic agent is a chlorhexidine compound.

6. The composition of claim 5 wherein said chlorhexidine compound is a salt of chlorhexidine selected from the group consisting of the gluconate, isethionate, formate, acetate, glutamate, succinamate, mono-diglycolate, di-methanesulfonate, lactate, diisobutyrate and glucoheptanate salt.

7. The composition of claim 6 wherein said chlorhexidine compound is chlorhexidine gluconate.

8. The composition of claim 4 wherein said composition includes conventional additives selected from perfumes, coloring agents and preservatives, isopropyl alcohol, ethyl alcohol, methyl p-hydroxybenzoate or propyl p-hydroxybenzoate, and pH adjusting agents and mixtures thereof.

9. The skin cleaning composition of claim 2 which consists essentially of about $5 \times 10^{-5}$ to 1.0 percent w/v of the antiseptic agent, $5 \times 10^{-4}$ to 4.0 percent w/v of said block copolymer, balance water.

10. The composition of claim 9 wherein said chlorhexidine compound is a salt of chlorhexidine selected from the group consisting of the gluconate, isethionate, formate, acetate, glutamate, succinimate, mono-diglycolate, di-methanesulfonate, lactate, diisobutyrate and glucoheptanate salt.

11. The composition of claim 10 wherein said chlorhexidine compound is chlorhexidine gluconate.

12. The composition of claim 9 wherein said composition includes conventional additives selected from perfumes, coloring agents and preservatives, isopropyl alcohol, ethyl alcohol, methyl p-hydroxybenzoate or propyl p-hydroxybenzoate, and pH adjusting agents and mixtures thereof.

* * * * *

UNITED STATES PATENT AND TRADEMARK OFFICE
CERTIFICATE OF CORRECTION

PATENT NO. : 4,326,977
DATED : April 27, 1982
INVENTOR(S) : Irving Rudolf Schmolka It is certified that error appears in the above—identified patent and that said Letters Patent is hereby corrected as shown below:

Claim 2, line 4, change formula to read as follows:

$$HO(C_2H_4O)_a(C_4H_8O)_b(C_2H_4O)_cH$$

Claim 2, line 3, delete "Ps" after the word "formula:"

*Signed and Sealed this*

*Twenty-ninth* Day of *June 1982*

[SEAL]

*Attest:*

GERALD J. MOSSINGHOFF

*Attesting Officer*     *Commissioner of Patents and Trademarks*